(12) United States Patent
Young

(10) Patent No.: US 9,462,803 B2
(45) Date of Patent: Oct. 11, 2016

(54) ORGAN PRESERVATION AND/OR PERFUSION

(71) Applicant: Philadelphia College of Osteopathic Medicine, Philadelphia, PA (US)

(72) Inventor: Lindon H. Young, Philadelphia, PA (US)

(73) Assignee: Philadelphia College of Osteopathic Medicine, Philadelphia, PA (US)

( * ) Notice: Subject to any disclaimer, the term of this patent is extended or adjusted under 35 U.S.C. 154(b) by 0 days.

(21) Appl. No.: 14/173,536

(22) Filed: Feb. 5, 2014

(65) Prior Publication Data

US 2014/0220549 A1 Aug. 7, 2014

Related U.S. Application Data

(62) Division of application No. 11/635,507, filed on Dec. 8, 2006, now abandoned.

(60) Provisional application No. 60/748,645, filed on Dec. 9, 2005.

(51) Int. Cl.
*A01N 1/00* (2006.01)
*A01N 1/02* (2006.01)

(52) U.S. Cl.
CPC .............. *A01N 1/0226* (2013.01); *A01N 1/02* (2013.01)

(58) Field of Classification Search
None
See application file for complete search history.

(56) References Cited

U.S. PATENT DOCUMENTS

| | | | |
|---|---|---|---|
| 4,798,824 A | 1/1989 | Belzer et al. | |
| 4,938,961 A | 7/1990 | Collins et al. | |
| 5,075,210 A * | 12/1991 | Wikman-Coffelt | 435/1.2 |
| 6,165,977 A | 12/2000 | Mochly-Rosen | |
| 2002/0150984 A1 | 10/2002 | Mochly-Rosen et al. | |
| 2003/0134774 A1 * | 7/2003 | Steinberg et al. | 514/1 |
| 2007/0148628 A1 | 6/2007 | Young | |
| 2014/0220549 A1 | 8/2014 | Young | |

FOREIGN PATENT DOCUMENTS

| | | |
|---|---|---|
| EP | 2056851 A1 | 5/2009 |
| EP | 2491941 A1 | 8/2012 |

OTHER PUBLICATIONS

Fujise et al (JBC, 269:50 31642-31648 (1994).*
Smits et (Drug Discovery Today, 1(3):273-278 (2004).*
Basso et al (Human Path., 31(8):98-998988-998.*
Basso et al (Human Path., 31(8):988-998 (2000).*
Armstrong, Cardiovas. Res., 61:427-436 (2004).*
Di-Capua et al, J. Neurochem., 84:409-412 (2003).*
Gray et al., JBC, 272(49):30945-30951 (1997).*
Inagaki, et al., Circ., 108:869-875 (2003).*
Inagaki et al., Circ., 108:2304-2307 (2003).*
Ping et al., Cir. Res., 88:59-62 (2001).*
Smits et (Drug Discovery Today, 1 (3):273-278 (2004).*
Maron et al (J. Am. College Cadrio., 54(9):866-875 (2009).*
Basso et al (Human Path., 31 (8):988-998 (2000).*
Schwartzkopff et al (JACC, 31 (5):1089-1096 (1998)).*
T. Eichholtz, et al., "A Myristoylated Pseudosubstrate Peptide, a Novel Proten Kinase C Inhibitor", The Journal of Biological Chemistry, 1993, vol. 268, No. 3, pp. 1982-1986.

\* cited by examiner

*Primary Examiner* — Thomas J Visone
(74) *Attorney, Agent, or Firm* — Blank Rome LLP

(57) ABSTRACT

The present invention relates to a solution for preservation, perfusion, and/or reperfusion of an organ, especially the heart, for transplantation. The solution contains peptide inhibitor(s) of protein kinase C ε (PKC ε). Methods for using the inventive solution are also disclosed, including methods for preserving an organ for transplantation, for protecting an ischemic organ from damage, for attenuating organ dysfunction after ischemia, for maintaining nitric oxide release and/or inhibiting superoxide release in an ischemic organ, and for protecting an organ from damage when isolated from the circulatory system.

14 Claims, 7 Drawing Sheets

ORGAN PRESERVATION AND/OR PERFUSION

The application is a divisional of U.S. patent application Ser. No. 11/635,507, filed Dec. 8, 2006, which claims priority from U.S. Provisional Patent Application Ser. No. 60/748,645, filed Dec. 9, 2005, the disclosure of which is incorporated herein by reference.

FIELD OF THE INVENTION

The present invention relates to a solution for preservation, perfusion, and/or reperfusion of an organ, especially the heart, for transplantation. The solution contains peptide inhibitor(s) of protein kinase ε (PKC ε).

BACKGROUND OF THE INVENTION

Successful organ transplantation is often limited due to ischemic/reperfusion injury. Isolated human hearts deprived of oxygen for more than four hours progressively loose vigor and often do not survive in recipient hosts. Other organs such as the kidney, liver, pancreas and lung are also subject to tissue and cellular damage when removed from their hosts prior to transplantation. This damage is due to hypoxic conditions and a lack of circulation, which normally delivers physiological concentrations of oxygen and nutrients, and removes toxic compounds produced by an organ's cells. Organ transplants have a higher frequency of success when performed immediately after excision from their hosts.

Recent advances have increased the rate of successful organ transplants and organ surgery, such as coronary bypass surgery. The first includes organ preservation and organ perfusion solutions. The second is improved methods and devices for the delivery of organ perfusion solutions to an organ.

Short-term myocardiac preservation is currently provided by cold storage after cardioplegic arrest. A variety of processes exist however differing by the composition of the solution used, the preservation temperature and the administration protocol. Different solutions for arresting and preserving the heart have been developed to protect the myocardium in cardiac surgery. Examples of these solutions include Krebs-Henseleit solution, UW solution, St. Thomas II solution, Collins solution and Stanford solution. (See, e.g., U.S. Pat. Nos. 4,798,824 and 4,938,961; Southard and Belzer, *Ann. Rev. Med.* 46:235-247 (1995); and Donnelly and Djuric, *Am. J. Hosp. Pharm.* 48:2444-2460 (1991)). Nevertheless, organ rejections still remains due to deterioration in the condition of the transplanted organ between the time of removal and the restoration of blood flow in the recipient.

Restoration of blood flow is the primary objective for treatment of organ tissue experiencing prolonged ischemia, e.g., during transplant. However, reperfusion of blood flow induces endothelium and myocyte injury, resulting in organ dysfunction (Buerke et al., *Am J Physiol* 266: H128-136, 1994; Lucchesi and Mullane, *Ann Rev Pharmacol Toxicol* 26: 2011-2024, 1986; and Lucchesi et al., *J Mol Cell Cardiol* 21: 1241-1251, 1989). The sequential events associated with reperfusion injury are initiated by endothelial dysfunction which is characterized by a reduction of the basal endothelial cell release of nitric oxide (NO) within the first 2.5-5 min post-reperfusion (Tsao and Lefer, *Am J Phyiol* 259: H1660-1666, 1990). The decrease in endothelial derived NO is associated with adhesion molecule up-regulation on endothelial and polymorphonuclear (PMN) leukocyte cell membranes (Ma et al., *Circ Res* 72: 403-412, 1993; and Weyrich et al., *J Leuko Biol* 57: 45-55, 1995). This event promotes PMN/endothelial interaction, which occurs by 10 to 20 min post-reperfusion, and subsequent PMN infiltration into the myocardium is observed by 30 min post reperfusion (Lefer and Hayward, In *The Role of Nitric Oxide in Ischemia-Reperfusion: Contemporary Cardiology*, Loscalzo et al. (Eds.), Humana Press, Totowa, N.J., pp. 357-380, 2000; Lefer and Lefer, *Cardiovasc Res* 32: 743-751, 1996; Tsao et al., *Circulation* 82: 1402-1412, 1990; and Weyrich et al., *J Leuko Biol* 57: 45-55, 1995).

Chemotactic substances released from reperfused tissue and plasma factors activate PMNs that augment PMN release of cytotoxic substances (i.e. superoxide anion) and contribute to organ dysfunction following ischemia/reperfusion (Lucchesi et al. *J Mol Cell Cardiol* 21: 1241-1251, 1989; Ma et al., *Circ Res* 69: 95-106, 1991; Tsao et al., *Circulation* 82: 1402-1412, 1990; and Tsao et al., *Am Heart J* 123: 1464-1471, 1992). Superoxide combines with NO to produce peroxynitrite anion thus reducing the bioavailability of NO and promotes endothelial dysfunction and PMN infiltration after myocardial ischemia/reperfusion (Clancey et al., *J Clin Invest* 90: 1116-1121, 1992; Hansen, *Circulation* 91: 1872-85, 1995; Lucchesi et al., *J Mol Cell Cardiol* 21: 1241-1251, 1989; Rubanyi and Vanhoutte, *Am J Physiol* 250: H815-821, 1986; Tsao et al., *Am Heart J* 123: 1464-1471, 1992; and Weiss, *New Eng J Med* 320: 365-375, 1989).

Therefore, there remains a need for a solution of improved quality that can extend the preservation time of an organ for transplantation and protect the organ from reperfusion injury after ischemia, so that the organ can resume proper function after restoration of blood flow.

SUMMARY OF THE INVENTION

The present invention provides a solution for preservation, perfusion, and/or reperfusion of an organ, especially the heart, containing peptide inhibitor(s) of protein kinase ε (PKC ε). The solution protects organ tissues and cells from damage while the organ is isolated from the circulatory system or is experiencing decreased blood flow (ischemia). The present inventor has discovered that the peptide inhibitors of protein kinase ε (PKC ε) can exert protective effects in organs undergoing ischemia/reperfusion.

In an embodiment, the solution contains about 1-10 μM, preferably about 1-5 μM, of the peptide inhibitor of PKC ε dissolved in a solution, preferably a saline solution.

The solution of the present invention can be used as a perfusion solution or a preservation solution. As a perfusion solution, it is pumped into the vasculature of the organ to protect the organ tissues and cells. As a preservation solution, it serves as a bathing solution into which the organ is submerged. Preferably, the organ is perfused with and submerged in the present solution. Further, the present solution also serves as a reperfusion solution upon restoration of blood flow to the organ after ischemia.

The present invention also include methods of using the solution of the present invention. These include methods for preserving an organ for transplantation, for protecting an ischemic organ from damage, for attenuating organ dysfunction after ischemia, and for protecting an organ from damage when isolated from the circulatory system.

DETAILED DESCRIPTION OF THE PREFERRED EMBODIMENT

Figure 1:
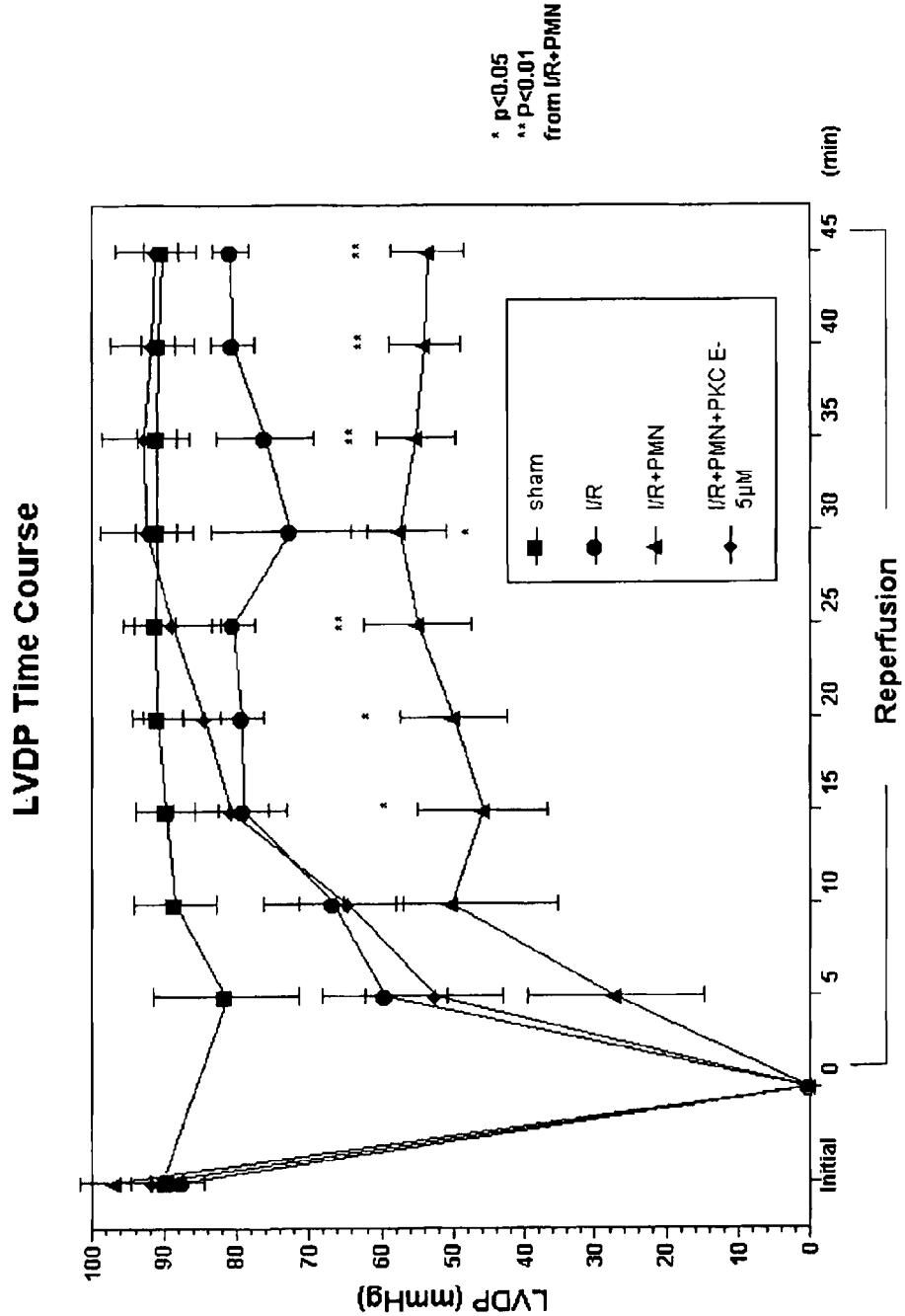
FIG. 1 is a graph showing the time course of LVDP (left ventricular developed pressure=left ventricular end systolic pressure (LVESP)–left ventricular end diastolic pressure (LVEDP)) in sham I/R, I/R, I/R+PMNs and I/R+PMN+PKC ε peptide inhibitor (5 μM) perfused rat hearts.

The present invention provides a solution for the preservation, perfusion, and/or reperfusion of an organ, especially the heart. The solution contains peptide inhibitor(s) of protein kinase ε (PKC ε). Preferably, the peptide inhibitor of PKC ε is present in the solution in an amount of about 1-10 μM, more preferably about 1-5 μM.

In a preferred embodiment, the peptide inhibitor of 1-10 μM, more preferably about 3-5 μM has an amino acid sequence of EAVSLKPT (SEQ ID NO: 1). Also, in other embodiments, it is preferred that the peptide inhibitor is myristoylated to facilitate better absorption into the cells of the organ. The myristoylation is preferably at the N-terminus of the peptide inhibitor.

In a preferred embodiment, the peptide inhibitor(s) are dissolved in a saline solution, preferably normal saline (0.9% NaCl). The peptide inhibitor(s) can also be dissolved in known preservation solution, such as Krebs-Henseleit solution, UW solution, St. Thomas II solution, Collins solution, Stanford solution, and the like. The solution may also contain one or more of sodium ($Na^+$), potassium ($K^+$), calcium ($Ca^{2+}$), magnesium ($Mg^{2+}$), glutamate, arginine, adenosine, manitol, allopurinol, glutathione, raffinose, and lactobionic acid in concentrations of about 4-7 mM, about 0.2-0.3 mM, about 108-132 mM, about 13-16 mM, about 18-22 mM, about 2-4 mM, about 0.5-1 mM, about 27-33 mM, about 0.9-1.1 mM, about 2.7-3.3 mM, about 25-35 mM, and about 80-120 mM, respectively. $Na^+$ can be in the form of NaOH; $K^+$ can be in the form of KCl and/or $KH_2PO_4$, most preferably at ratio of about 2-3.5 mM KCl and about 2-3.5 mM $KH_2PO_4$; $Ca^{2+}$ can be in the form of $CaCl_2$; and $Mg^{2+}$ can be in the form of $MgCl_2$. The solution may also contain one or more of peptide inhibitor(s) of protein kinase C βII (PKC βII), of protein kinase C ζ (PKC ζ), and peptide activator(s) of protein kinase C δ (PKC δ). The solution is preferably maintained at physiological pH of about 7.0-7.5, more preferably about 7.2-7.4.

The solution of the present invention can be used during all phases of an organ, especially the heart, transplant, including, but are not limited to, 1) isolating of the organ from the donor (cardioplegic solution); 2) preserving the organ (hypothermic storage/transport); and 3) re-implanting the organ in the recipient (reperfusion solution).

During perfusion or reperfusion, especially for the heart, it is preferred that the organ be perfused at a rate of about 1 mL/min for about 5 min. The perfusion rate can be varied, but it should not exceed about 25 mL/min. Overall, the perfusion rate should not be so high as to impose undue pressure on the vasculature of the organ.

The solution of the present invention can be prepared by 1) dissolving and diluting the peptide inhibitor(s) and the different constituents in distilled water; 2) adjusting the pH to about 7.2-7.4, e.g. with NaOH; and 3) sterilizing the solution, e.g., by filtering with a 0.2 μm filter. The sterilized solution is then kept isolated from contaminants in the environment.

Without further description, it is believed that one of ordinary skill in the art can, using the preceding description and the following illustrative examples, make and utilize the compounds of the present invention and practice the claimed methods. The following example is given to illustrate the present invention. It should be understood that the invention is not to be limited to the specific conditions or details described in this example.

EXAMPLE

Male Sprague Dawley rats (275-325 g, Ace Animals, Boyertown, Pa.) were anesthetized with 60 mg/kg pentobarbital sodium intraperitoneally (i.p.). Sodium heparin (1,000 U) was also administered i.p. The hearts were rapidly excised, the ascending aortas were cannulated, and retrograde perfusion of the heart was initiated with a modified Krebs buffer maintained at 37° C. at a constant pressure of 80 mmHg. The Krebs buffer had the following composition (in mmol/l): 17 dextrose, 120 NaCl, 25 $NaHCO_3$, 2.5 $CaCl_2$, 0.5 EDTA, 5.9 KCl, and 1.2 $MgCl_2$. The perfusate was aerated with 95% $O_2$ and 5% $CO_2$ and equilibrated at a pH of 7.3-7.4. The two side arms in the perfusion line proximal to the heart inflow cannula allowed PMNs, plasma without PKC ε peptide inhibitor (control hearts) or plasma containing different concentrations of PKC ε peptide inhibitor (1 or 5 μM) to be directly infused into the coronary inflow line. Coronary flow was monitored by a flow meter (T106, Transonic System, Inc., Ithaca, N.Y.). LVDP and $+dP/dt_{max}$ were monitored using a pressure transducer (SPR-524, Millar Instruments, Inc., Houston, Tex.), which was positioned in the left ventricular cavity. Hearts were immersed in a water-jacketed reservoir containing 160 mL of Krebs buffer maintained at 37° C. Coronary flow, LVDP and $+dP/dt_{max}$ were recorded using a Powerlab Station acquisition system (ADInstruments, Grand Junction, Colo.) in conjunction with a computer.

LVDP, $+dP/dt_{max}$, and coronary flow were measured every 5 min for 15 min to equilibrate the hearts and obtain a baseline measurement. LVDP was defined as left ventricular end-systolic pressure minus left ventricular end-diastolic pressure. After 15 min, the flow of the Krebs buffer was reduced to zero for 20 min to induce global ischemia. At reperfusion, hearts were infused for 5 min with $200 \times 10^6$ PMN resuspended in 5 mL of Krebs buffer plus 5 mL of plasma at a rate of 1 mL/min. In some experiments, PKC ε peptide inhibitor (Genemed Synthesis, Inc., San Francisco, Calif.) was added to plasma at a final concentration of 1 or 5 μM. Sham I/R hearts were not subjected to ischemia and were not perfused with PMNs.

The following groups of isolated perfused rat hearts were used:

Group 1: Sham I/R hearts were not subjected to ischemia and were not perfused with PMNs, but were perfused with 5 mL of plasma (1 mL/min) at 35 minutes into perfusion (the same time point that I/R hearts would be given 5 mL of plasma, 15 minutes of baseline recordings plus 20 minutes ischemia). These hearts represented a control group to determine if the isolated rat heart can maintain LVDP and $+dP/dt_{max}$ throughout the 80-minute protocol (n=6).

Group 2: Sham I/R+PKC ε peptide inhibitor (5 μM) hearts were not subjected to ischemia and not perfused with PMNs. These hearts were administered the PKC ε peptide inhibitor (5 μM, dissolved in plasma from a 5 mM stock in $H_2O$) 35 minutes into perfusion. This group was employed to determine if the PKC ε peptide inhibitor causes a cardiotonic or cardiodepressant effect (n=6).

Group 3: I/R hearts were subjected to 20 min of ischemia and perfused with 5 mL of plasma (1 mL/min) during the first 5 min of reperfusion, but were not perfused with PMNs. These hearts represented a control group to determine if 20 min of ischemia followed by reperfusion stunned the heart, but LVDP and $+dP/dt_{max}$ will recover to baseline values (initial) by the end of the 45-minute reperfusion period (n=7).

Group 4: I/R+PKC ε peptide inhibitor (5 μM, dissolved in plasma) hearts were subjected to 20 min of ischemia and not perfused with PMNs. These hearts were perfused with 5 mL of plasma+PKC ε peptide inhibitor during the first 5 min of reperfusion. This group was employed to determine if the PKC ε peptide inhibitor causes a cardiodepressant effect in the setting of I/R without PMNs (n=6).

Group 5: I/R+PMNs hearts were subjected to 20 min of ischemia and perfused with 5 mL of plasma (1 mL/min) and PMNs (resuspended in 5 mL Krebs buffer) during the first 5 min of reperfusion. These hearts represented a control group to determine if 20 min of ischemia followed by 45 min reperfusion in the presence of PMNs ($200 \times 10^6$) resulted in a sustained cardiac contractile dysfunction throughout the 45 min reperfusion period compared to initial baseline values (n=7).

Group 6: I/R+PMNs+PKC ε peptide inhibitor (1 μM) hearts were subjected to 20 min of ischemia and perfused with 1 μM PKC ε peptide inhibitor (dissolved in plasma) and PMNs ($200 \times 10^6$) during the first 5 minutes of reperfusion. These hearts represented a group to determine the effect of PKC ε inhibition in attenuating PMN-induced cardiac contractile dysfunction (n=6).

Group 7: I/R+PMNs+PKC ε peptide inhibitor (5 μM) hearts were subjected to 20 min of ischemia and perfused with 5 μM PKC ε peptide inhibitor (dissolved in plasma) and PMNs ($200 \times 10^6$) during the first 5 minutes of reperfusion. These hearts represented a group to determine the effect of PKC ε inhibition at a higher concentration of the PKC ε peptide inhibitor in attenuating PMN-induced cardiac contractile dysfunction (n=6).

FIG. 1 showed the time course of cardiac contractile function (LVDP) for the sham I/R, I/R, I/R+PMN and I/R+PMN+PKC ε peptide inhibitor (5 μM) groups, and illustrated the changes in LVDP during the 80 min perfusion period. The hearts in the sham I/R group remained at 100±2% of initial baseline values of LVDP for the entire duration of the perfusion period. Hearts in the I/R group experienced a depression in LVDP during the initial stages of reperfusion, but by the end of reperfusion they had recovered to 92±3% of initial baseline values. However, the hearts in the I/R+PMN group exhibited severe cardiac contractile dysfunction, only recovering to 55±5% of initial baseline values by the end of reperfusion. By contrast, the hearts in the I/R+PMN+PKC ε peptide inhibitor (5 μM) recovered markedly in LVDP by 15 min post-reperfusion (88±9% of initial baseline values) and continued to improve throughout the 45 min reperfusion period and recovered to 99±6% of initial baseline values.

Figure 2:
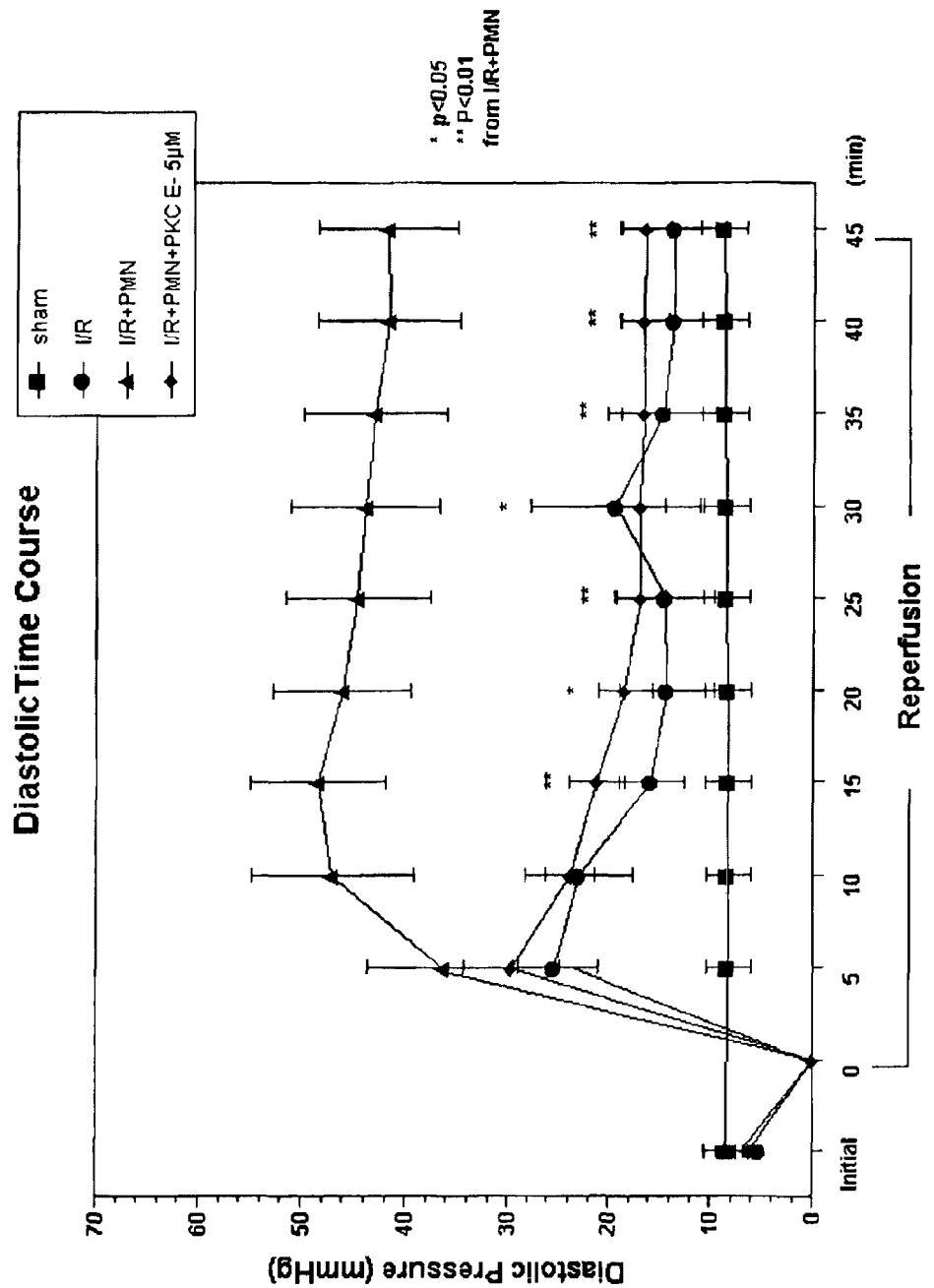
FIG. 2 is a graph showing LVEDP timecourse in sham I/R, I/R, I/R+PMN and I/R+PMN+PKC ε peptide inhibitor (5 μM) groups.

The significant differences between the PKC ε inhibitor treated hearts and control I/R+PMN hearts observed in the LVDP timecourse can be most attributed to the end diastolic pressure (LVEDP). FIG. 2 is the LVEDP timecourse in sham I/R, I/R, I/R+PMN and I/R+PMN+PKC ε peptide inhibitor (5 μM) groups. There were no significant differences in initial LVEDP (5-8 mmHg). However, significant differences were observed between control I/R+PMN and I/R+PMN+PKC ε inhibitor treated hearts as early as 15 min post-reperfusion and this difference was sustained throughout the 45 min reperfusion. Control I/R+PMN hearts had a final LVEDP of 42±7 mmHg compared to I/R+PMN+PKC ε inhibitor treated hearts that had a final LVEDP of 16±2 mmHg, and this difference was significant (p<0.01).

In order to establish whether the PKC ε peptide inhibitor produced any direct inotropic effects on cardiac contractile function, Sham I/R hearts were perfused with PKC ε peptide inhibitor (5 μM). This group served as one of the controls for the study. These hearts did not show any significant change in LVDP (FIG. 3) or +dP/dt$_{max}$ (FIG. 4) at the end of the 80 min. reperfusion period, thus, indicating that at this dose the PKC ε peptide inhibitor had no direct effect on cardiac contractile function.

Figure 3:
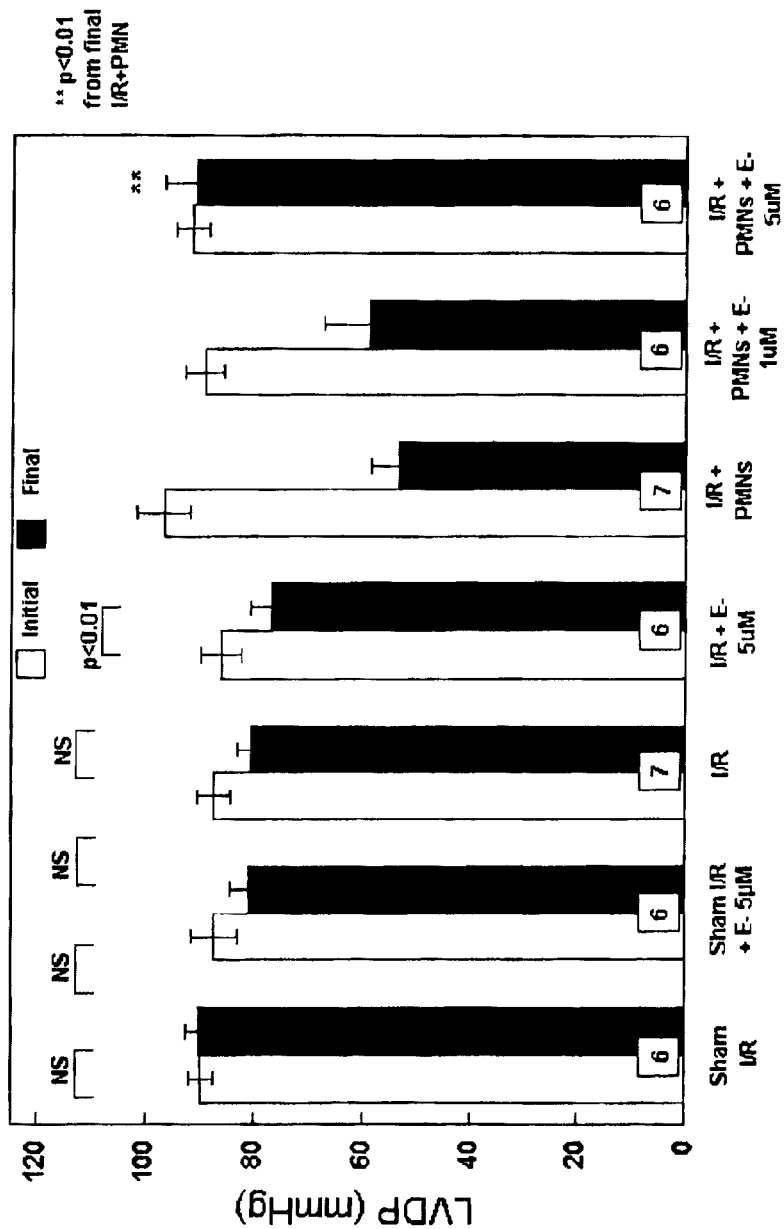
FIG. 3 is a graph showing initial and final LVDPs expressed in mmHg from isolated perfused rat hearts before ischemia (I) (Initial) and after 45 min post reperfusion (Final). Hearts were perfused in the presence or absence or PMNs. PMNs induced a significant contractile dysfunction, which was attenuated by the PKC ε peptide inhibitor. All values are expressed as mean±SEM. Numbers of hearts examined are at the bottom of the bars.
Figure 4:
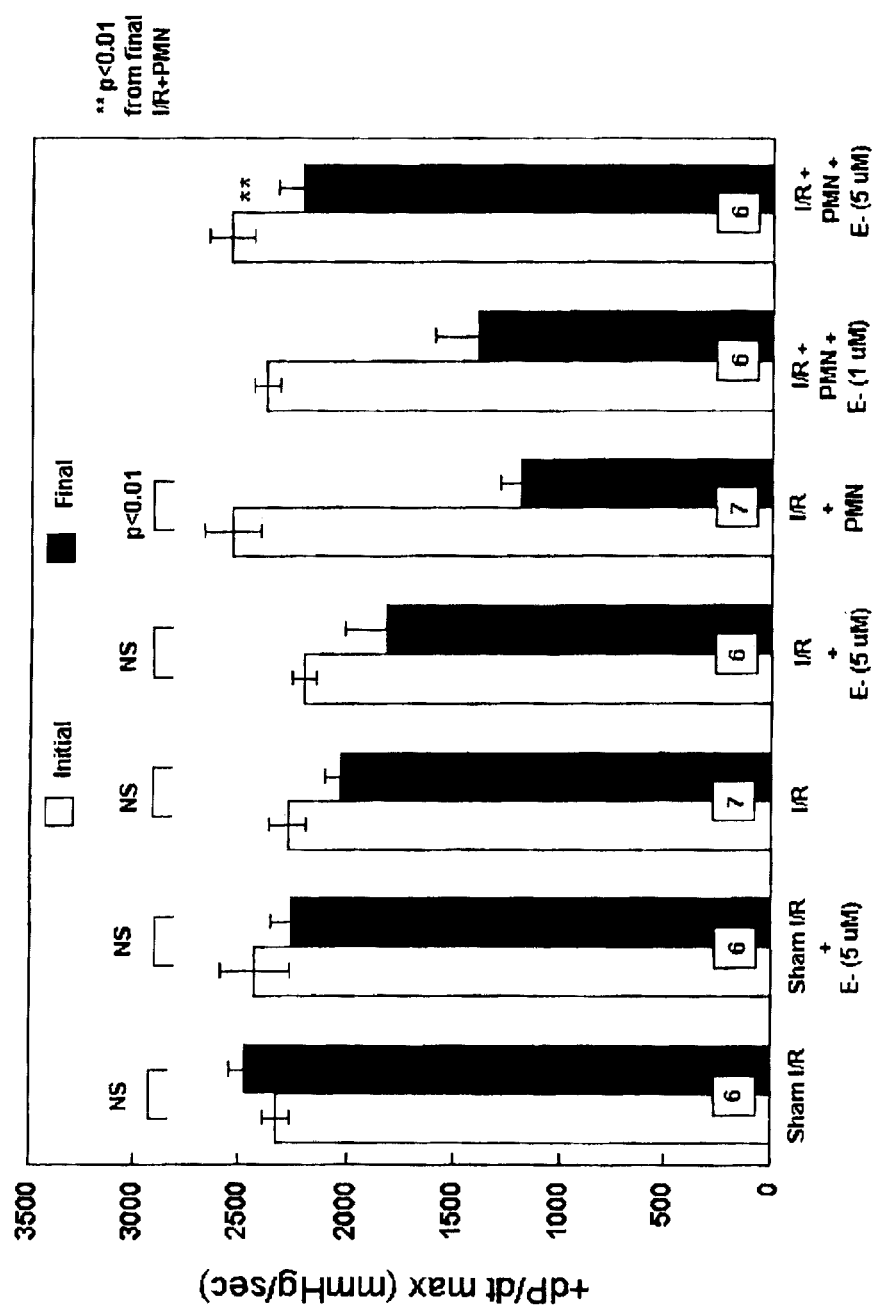
FIG. 4 is a graph showing initial and final maximal rates of LVDP (+dP/dt max) expressed in mmHg/s in isolated perfused rat hearts before ischemia (Initial) and after reperfusion (Final). Hearts were perfused in the presence or absence of PMNs. PMNs induced a significant contractile dysfunction, which was attenuated by the PKC ε peptide inhibitor. All values are expressed as means±SEM. Numbers of hearts examined are at the bottom of the bars.

FIGS. 3 and 4 showed the initial and final values for LVDP and +dP/dt$_{max}$ from isolated perfused hearts respectively. There was no significant difference between the initial baseline values of all the groups studied. There was also no significant difference between the initial and final values of LVDP and +dP/dt$_{max}$ for the Sham I/R, I/R, Sham I/R+PKC ε peptide inhibitor and I/R+PKC ε peptide inhibitor (5 μM) groups. However, there was a significant difference between the initial and final values of LVDP and +dP/dt$_{max}$ for the I/R+PMN group. A significant decrease (p<0.01) from initial baseline of 55±5% in LVDP and 47±4% in +dP/dt$_{max}$ at 45 min post-reperfusion was observed.

The 5 μM dose the was the most cardioprotective as the hearts in the I/R+PMN+PKC ε peptide inhibitor (5 μM) recovered to 99±6% and 87±5% of initial baseline at 45 min. post-reperfusion for LVDP and +dP/dt$_{max}$, respectively. These values were significantly different from I/R+PMN at 45 min. post-reperfusion (p<0.01). The 1 μM dose of PKC ε peptide inhibitor was not cardioprotective as the hearts in the I/R+PMN+PKC ε peptide inhibitor (1 μM) group only recovered to 66±9% and 59±9% for LVDP and +dP/dt$_{max}$ respectively. The final values of LVDP and +dP/dt$_{max}$ at the 1 μM dose group were not significantly different from the final values of the I/R+PMN group.

Figure 5:
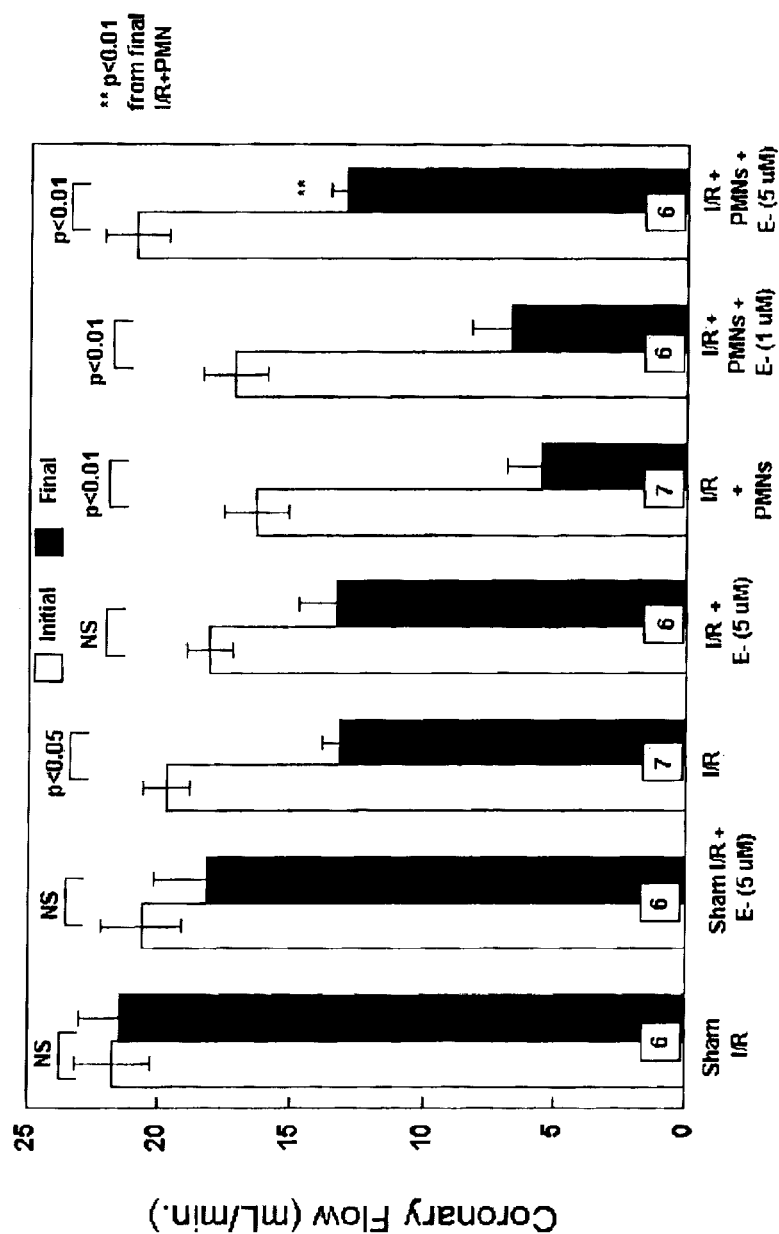
FIG. 5 is a graph showing coronary flows among the seven groups in the cardiac function experiments (sham I/R, sham I/R+PKC ε peptide inhibitor (5 μM), I/R, I/R+PKC ε peptide inhibitor (5 μM), I/R+PMNs, and I/R+PMN+PKC ε peptide inhibitor (1 and 5 μM)).

FIG. 5 illustrates the coronary flow among the seven groups in the cardiac function experiments. There were no significant differences in initial coronary flow (16-21 ml/min). The control I/R+PMN groups only recovered to 34±8% of initial baseline whereas, the I/R+PMN ε inhibitor treated hearts recovered to 62±3% of initial baseline and this difference was significant (p<0.01).

Figure 6:
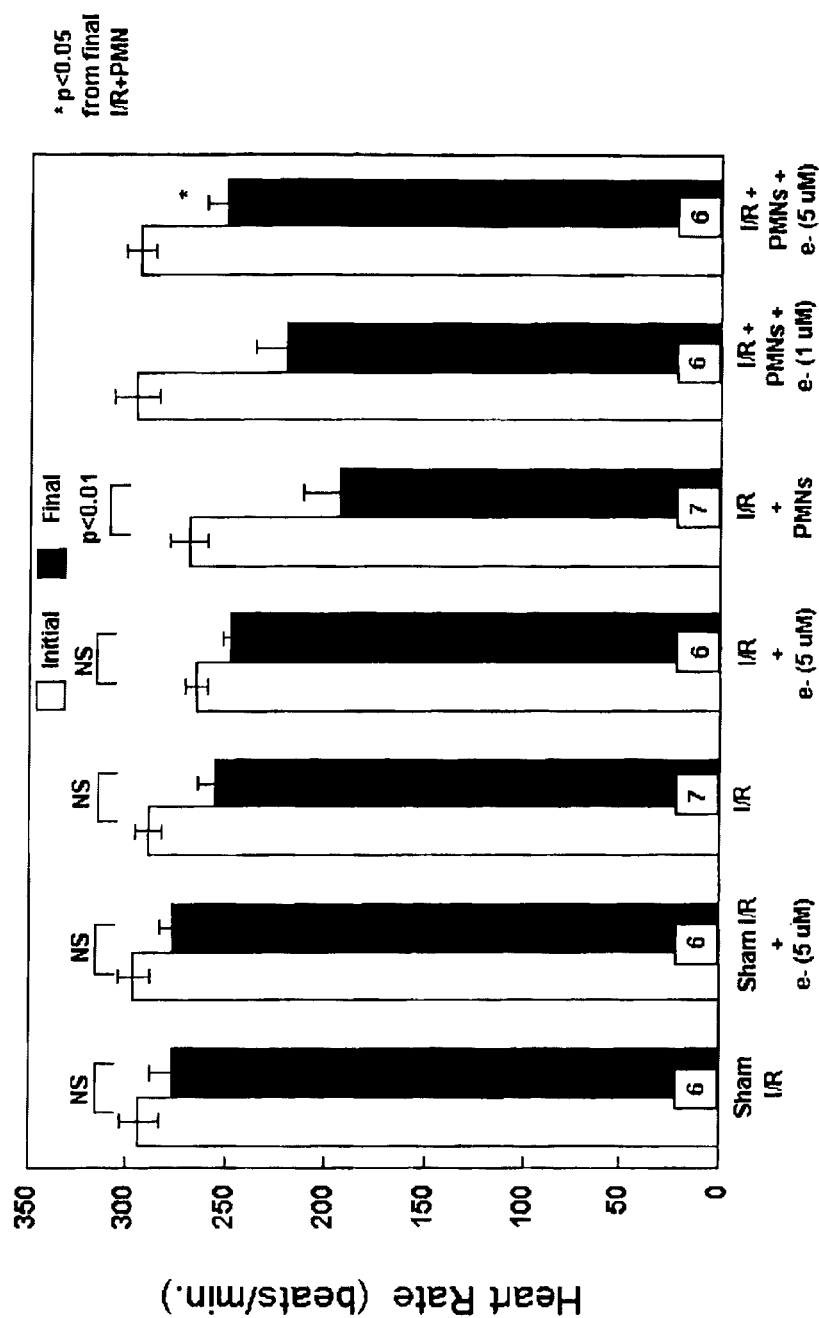
FIG. 6 is a graph showing heart rates among the seven groups in the cardiac function experiments (sham I/R, sham I/R+PKC ε peptide inhibitor (5 μM), I/R, I/R+PKC ε peptide inhibitor (5 μM), I/R+PMNs, and I/R+PMN+PKC ε peptide inhibitor (1 and 5 μM)).

FIG. 6 illustrates the heart rate among the seven groups in the cardiac function experiments. There were no significant differences in initial heart rate (295-265 beats/min). The control I/R+PMN groups only recovered to 72±7% of initial baseline whereas, the I/R+PMN_PKC ε inhibitor treated hearts recovered to 85±4% of initial baseline and this difference was significant (p<0.05).

Figure 7:
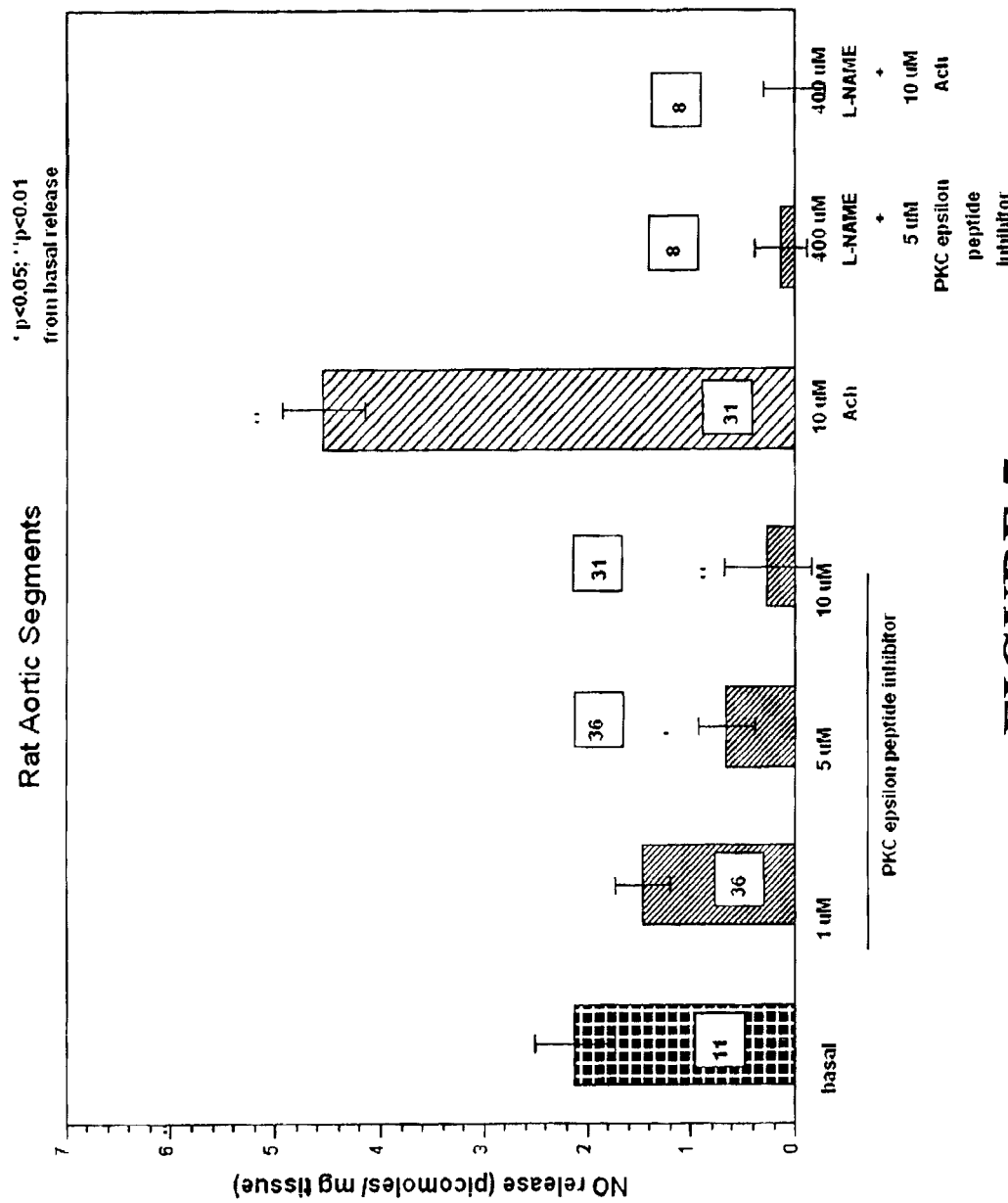
FIG. 7 is a graph showing NO release from rat aortic endothelium in untreated (basal) segments compared to PKC ε peptide inhibitor treated segments (1, 5, and 10 μM).

FIG. 7 illustrates the NO release from rat aortic endothelium in untreated (basal) segments compared to PKC ε peptide inhibitor treated segments (1-10 μM). Acetylcholine (Ach) (10 μM) was used as a positive control. There was a dose-response effect of PKC ε peptide inhibitor treated segments that significantly inhibited the basal NO release from 2.12±0.39 pmoles/mg tissue to 0.66±0.28 (5 μM; p<0.05) and 0.26±0.42 (10 μM) pmoles/mg tissue. Although augmenting endothelial derived NO is usually associated with cardioprotection following I/R, it is speculated that the enzyme responsible for endothelial NO release (eNOS) may shift its product profile to the production of superoxide release when the substrate (L-arginine) or co-factor (BH$_4$) is not readily available during early reperfusion.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A method for protecting an organ from reperfusion injury after ischemia, said method comprising the step of reperfusing the organ with a solution containing an inhibitor of protein kinase ε consisting of the amino acid sequence of SEQ ID NO: 1.

2. The method of claim 1, wherein the solution is a saline solution.

3. The method of claim 1, wherein the solution further comprises potassium chloride.

4. The method of claim 1, wherein the inhibitor of protein kinase ε consisting of the amino acid sequence of SEQ ID NO: 1 is about 1-10 μM in concentration.

5. The method of claim 1, wherein the organ is a heart.

6. The method of claim 1, wherein the organ is a mammalian organ.

7. The method of claim 6, wherein the organ is a human organ.

8. The method of claim 1, wherein the organ is preserved for transplantation.

9. The method of claim 1, wherein the inhibitor of protein kinase ε consisting of the amino acid sequence of SEQ ID NO: 1 is myristoylated.

10. The method of claim 1, further comprising the step of submerging the organ in the solution containing the inhibitor of protein kinase ϵ consisting of the amino acid sequence of SEQ ID NO: 1.

11. The method of claim 1, wherein the step of reperfusing the organ takes place at a rate of less than about 20 mL/minute.

12. The method of claim 1, wherein the step of reperfusing the organ takes place at a rate of about 1 mL/minute.

13. The method of claim 1, wherein the step of reperfusing the organ is a retrograde perfusion.

14. The method of claim 1, wherein the step of reperfusing the organ lasts about 5 minutes.

\* \* \* \* \*

```
SEQUENCE LISTING

<160> NUMBER OF SEQ ID NOS: 1

<210> SEQ ID NO 1
<211> LENGTH: 8
<212> TYPE: PRT
<213> ORGANISM: Homo sapiens

<400> SEQUENCE: 1

Glu Ala Val Ser Leu Lys Pro Thr
1               5
```